(12) United States Patent
Mann et al.

(10) Patent No.: US 6,254,586 B1
(45) Date of Patent: *Jul. 3, 2001

(54) METHOD AND KIT FOR SUPPLYING A FLUID TO A SUBCUTANEOUS PLACEMENT SITE

(75) Inventors: Alfred E. Mann, Beverly Hills; John J. Mastrototaro, Los Angeles; Clifford W. Hague, Sherman Oaks, all of CA (US)

(73) Assignee: MiniMed Inc., Northridge, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/395,530

(22) Filed: Sep. 14, 1999

Related U.S. Application Data

(63) Continuation-in-part of application No. 09/161,128, filed on Sep. 25, 1998, now Pat. No. 5,951,521.

(51) Int. Cl.$^7$ ............................................. A61M 31/00
(52) U.S. Cl. ..................... 604/506; 604/44; 604/180; 604/244; 600/347; 206/365
(58) Field of Search ........................... 206/364, 365, 206/570; 604/27, 43, 44, 48, 244, 256, 264, 272, 284, 541, 174, 180, 93.01, 500, 506; 600/345, 347, 372, 373, 377

(56) References Cited

U.S. PATENT DOCUMENTS

| | | |
|---|---|---|
| 3,841,307 * | 10/1974 | Friedell ............................... 128/2 G |
| 4,562,751 | 1/1986 | Nason et al. . |
| 4,573,994 | 3/1986 | Fischell et al. . |
| 4,678,408 | 7/1987 | Nason et al. . |
| 4,685,903 | 8/1987 | Cable et al. . |
| 4,810,246 * | 3/1989 | Frisch et al. ............................ 604/93 |
| 4,966,582 * | 10/1990 | Sit et al. ................................ 604/86 |
| 5,299,571 | 4/1994 | Mastrototaro . |
| 5,390,671 | 2/1995 | Lord et al. . |
| 5,391,250 | 2/1995 | Cheney, II et al. . |
| 5,482,473 | 1/1996 | Lord et al. . |
| 5,586,553 * | 12/1996 | Halili et al. .......................... 128/635 |
| 5,951,521 * | 9/1999 | Mastrototaro et al. .............. 604/174 |

* cited by examiner

Primary Examiner—Anhtuan T. Nguyen
Assistant Examiner—Jeremy Thissell
(74) Attorney, Agent, or Firm—MiniMed Inc.

(57) ABSTRACT

There is provided a method of supplying a fluid to a placement site. For instance, a sensor set is first mounted onto a skin of a user, and a placement site is contacted with the sensor set. The sensor set includes a base to secure the sensor set to the skin of the user; a cannula coupled to and extending from the base; an insertion device operatively coupled to the sensor set and the cannula to facilitate insertion of the cannula to contact the placement site; an externally extending conduit; and a sensor. The cannula has at least one lumen with an end for fluid communication with the placement site, and also has at least one port formed near another end of the lumen opposite the end for fluid communication. The conduit is in fluid communication with the at least one port of the cannula. The sensor has a sensor portion exposed by the at least one port in the at least one lumen of the cannula to determine a body characteristic of the user at the placement site. After the sensor set is mounted on the user's skin, a fluid is introduced through the externally extending conduit and the lumen to the placement site. Kits for carrying out the inventive methods are also provided.

45 Claims, 6 Drawing Sheets

METHOD AND KIT FOR SUPPLYING A FLUID TO A SUBCUTANEOUS PLACEMENT SITE

RELATED APPLICATIONS

This is a continuation-in-part of U.S. patent application Ser. No. 09/161,128, to Mastrototaro et al., filed Sep. 25, 1998, now U.S. Pat. No. 5,951,521 which is incorporated herein in its entirety by reference.

FIELD OF THE INVENTION

This invention relates to improved sensor placement and infusion devices and, in particular embodiments, to devices and methods for placing a sensor set at a selected insertion site within the body of a user, which has the capability to remove fluid buildups and/or deliver selected fluids to the selected insertion site. The invention further relates to methods for delivering a fluid to the selected insertion site, and to kits for carrying out the delivery methods.

BACKGROUND OF THE INVENTION

Over the years, a variety of implantable electrochemical sensors have been developed for detecting and/or quantifying specific agents or compositions in a patient's blood. For instance, glucose sensors have been developed for use in obtaining an indication of blood glucose levels in a diabetic patient. Such readings can be especially useful in monitoring and/or adjusting a treatment regimen which typically includes the regular administration of insulin to the patient. Thus, blood glucose readings are particularly useful in improving medical therapies with semi-automated medication infusion pumps of the external type, as generally described in U.S. Pat. Nos. 4,562,751; 4,678,408; and 4,685,903; or automated implantable medication infusion pumps, as generally described in U.S. Pat. No. 4,573,994, which are herein incorporated by reference.

Generally, small and flexible electrochemical sensors can be used to obtain periodic readings over an extended period of time. In one form, flexible subcutaneous sensors are constructed in accordance with thin film mask techniques in which an elongated sensor includes thin film conductive elements encased between flexible insulative layers of polyimide sheets or similar material. Such thin film sensors typically include a plurality of exposed electrodes at one end for subcutaneous placement with a user's blood, or the like, and a corresponding exposed plurality of conductive contacts at another end for convenient external electrical connection with a suitable monitoring device. Typical thin film sensors are described in commonly assigned U.S. Pat. Nos. 5,390,671; 5,391,250; 5,482,473; and 5,586,553 which are incorporated by reference herein. See also U.S. Pat. No. 5,299,571.

Drawbacks to conventional implantable sensors arise from the initial subcutaneous insertion and from the extended presence of the sensor at the subcutaneous insertion site. For example, the area surrounding the implantable sensor may swell or fill with fluid that impedes the ability of the implantable sensor to provide accurate results. This represents a potential health hazard, since less accurate information could lead to erroneous dosing of medication or the like. Another drawback that results from a sensor being inserted for extended periods of time is that it is more prone to infection, which is a health hazard and can also result in fluid buildup and inaccurate readings. To overcome these drawbacks of inaccurate readings and the possibility of infection, the implantable sensor is removed from the subcutaneous site and a new implantable sensor is inserted at a different subcutaneous insertion site. While this solution does provide more accurate readings or reduces the occurrence of infections, it is expensive due to the increased number of implantable sensors needed, and is painful for the user who must insert implantable sensors in more locations and on a more frequent basis.

In addition to addressing problems of fluid buildup at a subcutaneous insertion site, it would be beneficial to supply a fluid to the site. In particular, it would be useful to supply fluids including antibiotics, anti-inflammatory agents or healing agents to the insertion site. It would also be beneficial to supply a calibration solution to a sensor at the insertion site, to enable sensor calibration in situ and thus obviate the need for frequent removal of the implanted sensor.

A need exists for a method of delivering a fluid to an insertion site, in particular a sensor insertion site. There is also a need for a kit including elements that are useful in carrying out the improved method.

SUMMARY OF THE DISCLOSURE

In accordance with one aspect of the present invention, there is provided a method of supplying a fluid to a placement site. According to the inventive method, a sensor set is first mounted onto a skin of a user, and a placement site is contacted with the sensor set. The sensor set includes a base to secure the sensor set to the skin of the user; a cannula coupled to and extending from the base; an insertion device operatively coupled to the sensor set and the cannula to facilitate insertion of the cannula to contact the placement site; an externally extending conduit; and a sensor. The cannula has at least one lumen with an end for fluid communication with the placement site, and also has at least one port formed near another end of the lumen opposite the end for fluid communication. The conduit is in fluid communication with the at least one port of the cannula. The sensor has a sensor portion exposed by the at least one port in the at least one lumen of the cannula to determine a body characteristic of the user at the placement site.

After the sensor set is mounted on the user's skin, a fluid is introduced through the externally extending conduit and the lumen to the placement site.

In a preferred embodiment, the fluid is supplied periodically in a predetermined amount, more specifically from an external pump device. Alternatively, the fluid is supplied from a disposable source.

Preferred fluids for delivery to the placement site include an ingredient such as a healing agent, an antibiotic, an anti-inflammatory agent, a cleaning agent, a sensor recharging agent, an insulin, an insulin analog, saline or glucose. According to a specific preferred embodiment, the fluid is a calibration solution having a known level of the body characteristic of the user. More particularly, the body characteristic is the glucose level in a bodily fluid (e.g., blood or interstitial fluid) of the user, and the calibration solution includes a predetermined concentration of glucose.

In accordance with another aspect of the present invention, a method of supplying a fluid to a placement site includes the step of mounting the sensor set onto a skin of a user and contacting a placement site. The sensor set includes a base, a cannula and a sensor as described above. Next, the fluid is introduced through the port of the lumen to the placement site.

In a preferred embodiment, the sensor set further includes an insertion device operatively coupled to the sensor set and the cannula to facilitate insertion of the cannula to contact the placement set.

A more specific preferred embodiment of the foregoing method employs a sensor set that further includes a septum disposed adjacent to the at least one port of the cannula. The fluid is introduced through the septum and the lumen to the placement site.

Another more specific preferred embodiment of the foregoing method employs a sensor set that further includes an externally extending conduit in fluid communication with the at least one port of the cannula. In this embodiment, the fluid is introduced through the externally extending conduit and the lumen to the placement site.

In accordance with a further aspect of the present invention, a method of supplying a fluid to a placement site includes the steps of mounting a sensor set onto a skin of a user and contacting the placement site. The sensor set includes a base, a cannula, an externally extending conduit, and a sensor, as described herein. Next, fluid is introduced through the externally extending conduit and the lumen to the placement site.

In accordance with yet another aspect of the present invention, a method of calibrating a sensor which is placed at a placement site and which is adapted to determine a body characteristic of a user is provided. According to the inventive method, a sensor set is first mounted onto a skin of a user, and the placement site is contacted. The sensor set includes a base, a cannula and an insertion device as described above, and a sensor. The sensor has a connection portion coupled to the sensor set, and a sensor portion exposed by the at least one port in the at least one lumen of the cannula to determine the characteristic of the user at the placement site. Next, the connection portion of the sensor is electrically connected to a monitor for monitoring the characteristic of the user. A predetermined quantity of a calibration solution having a known level of the characteristic of the user is then introduced through the externally extending conduit to the sensor portion of the sensor, causing a sensor output to be generated and subsequently detected by the monitor. Finally, the sensor is calibrated using the sensor output.

Kits that are useful in carrying out the inventive methods are also provided. Thus, according to an additional aspect of the present invention, there are provided kits for supplying fluid to a placement site that includes sensor sets as described above; sources of fluid to be supplied to the placement site; and a delivery device by which the fluid is introduced to the placement site via the sensor sets.

According to a preferred embodiment, the source of fluid is an external pump. In another preferred embodiment, the source of fluid is a disposable bubble or blister set. Alternatively, the source of fluid is a container of fluid and wherein the delivery device is a syringe.

In more specific embodiments, the sensor of the sensor set has a connection portion coupled to the set, and the kit further includes a monitor that is electrically connectable to the connection portion of the sensor.

Kits are also provided according to the invention for calibrating a sensor which is placed at a placement site and which is adapted to determine a body characteristic of a user. According to this aspect of the present invention, the kits include a sensor set as described herein; a source of a predetermined quantity of a calibration solution having a known level of the characteristic of the user; and a delivery device by which the predetermined quantity of the calibration solution is introduced via the sensor set to the sensor at the placement site.

In a more specific preferred embodiment, the sensor of the sensor set has a connection portion coupled to the sensor set, and the kit further includes a monitor that is electrically connectable to the connection portion of the sensor.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

DETAILED DESCRIPTION OF THE PREFERRED EMBODIMENTS

Figure 1:
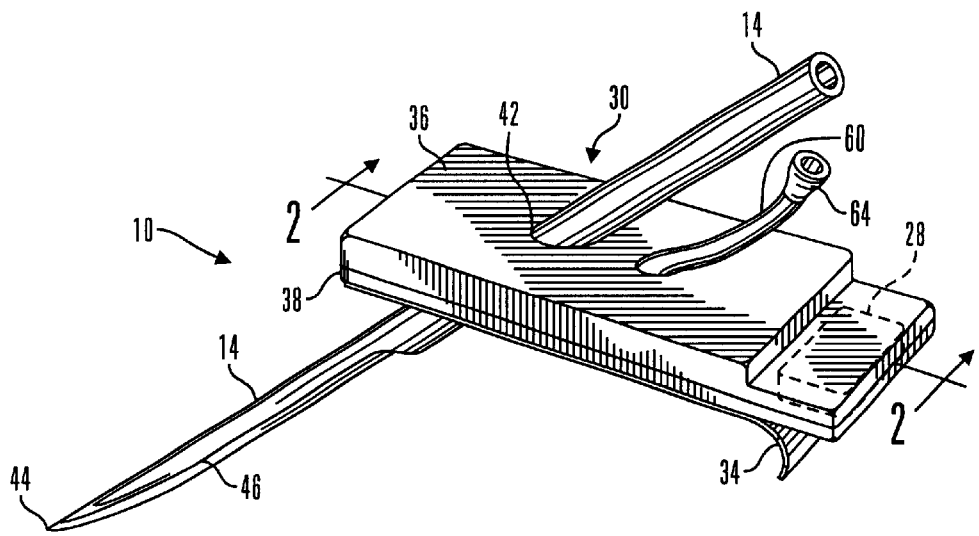
FIG. 1 is a is a perspective view illustrating a subcutaneous sensor insertion set embodying the novel features of the invention.

As shown in the drawings for purposes of illustration, the invention is embodied in a sensor set that includes a sensor that is coupled to a monitor for determining body characteristics. In preferred embodiments of the present invention, the sensor set and monitor are for determining glucose levels in the blood and/or bodily fluids of the user, and the sensor set is capable of reducing the build up of fluid surrounding the sensor. However, it will be recognized that further embodiments of the invention may be used to determine the levels of other agents, characteristics or compositions. In other embodiments, the sensor set may also include the capability to introduce fluids or compositions into the area surrounding the sensor set and sensor. The sensor set and sensor are primarily adapted for use in subcutaneous human tissue. However, still further embodiments may be placed in other types of tissue, such as dermal, subdermal, intraperitoneal and peritoneal tissues, and other tissues including muscle tissue, lymphatic nodes, other organ tissues or the like. Yet other embodiments may be used in animal tissue.

As shown in FIG. 1, an improved sensor set 10 is provided for placement of a flexible sensor 12 (see FIG. 2), or the like, at a selected site in the body of a user. The sensor set 10 includes a hollow, slotted insertion needle 14, and a cannula 16. The needle 14 is used to facilitate quick and easy subcutaneous placement of the cannula 16 at the insertion site (or placement site). The cannula 16 includes a sensor portion 18 of the sensor 12 to expose one or more sensor electrodes 20 to the user's bodily fluids through a window 22 formed in the cannula 16. After insertion, the insertion needle 14 is withdrawn to leave the cannula 16 with the sensor portion 18 and the sensor electrodes 20 in place at the selected insertion site.

In preferred embodiments, the sensor set 10 facilitates accurate placement of a flexible thin film electrochemical sensor 12 of the type used for monitoring specific blood parameters representative of a user's condition. The sensor set 10 is designed to place the sensor 12 subcutaneously, or at another selected site within the body of a user, in a manner minimizing patient discomfort and trauma. In preferred embodiments, the sensor 12 monitors blood glucose levels, and may be used in conjunction with automated or semi-automated medication infusion pumps of the external or implantable type as described in U.S. Pat. No. 4,562,751; 4,678,408; 4,685,903 or 4,573,994, to deliver insulin to a diabetic patient.

Preferred embodiments of the flexible electrochemical sensor 12 are constructed in accordance with thin film mask techniques to include elongated thin film conductors embedded or encased between layers of a selected insulative material such as polyimide film or sheet. The sensor electrodes 20 at a tip end of the sensor portion 18 are exposed through one of the insulative layers for direct contact with patient blood, or other bodily fluids, when the sensor 12 is subcutaneously placed at an insertion site. The sensor portion 18 is joined to a connection portion 24 (see FIG. 2) that terminates in conductive contact pads, or the like, which are also exposed through one of the insulative layers. As is known in the art, and illustrated schematically in FIG. 2, the connection portion 24 and the contact pads are adapted for electrical connection to a suitable monitor 26 for monitoring a user's condition in response to signals derived from the sensor electrodes 20. Further description of flexible thin film sensors of this general type is found in U.S. Pat. No. 5,391,250, entitled METHOD OF FABRICATING THIN FILM SENSORS, which is herein incorporated by reference. The connection portion 24 may be conveniently connected electrically to the monitor 26 by a connector block 28 (or the like) as shown and described in U.S. Pat. No. 5,482,473, entitled FLEX CIRCUIT CONNECTOR, which is also herein incorporated by reference.

Figure 2:
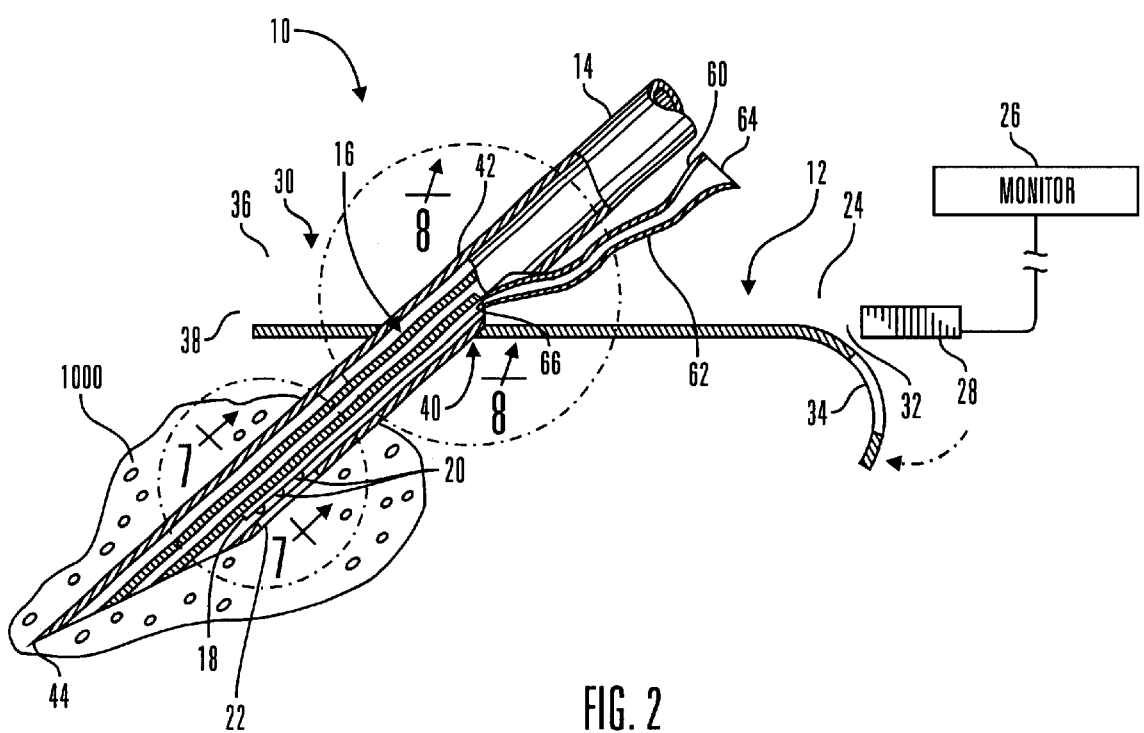
FIG. 2 is an enlarged longitudinal vertical section taken generally on the line 2—2 of FIG. 1.
Figure 3:
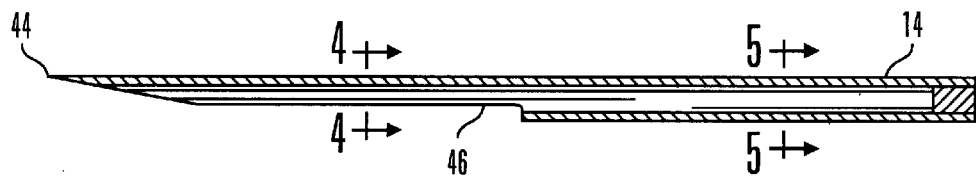
FIG. 3 is an enlarged longitudinal sectional of a slotted insertion needle used in the insertion set of FIGS. 1 and 2.
Figure 4:
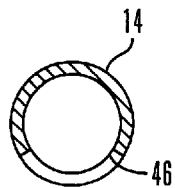
FIG. 4 is an enlarged transverse section taken generally on the line 4—4 of FIG. 3.
Figure 5:
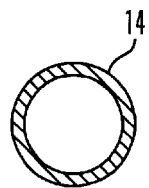
FIG. 5 is an enlarged transverse section taken generally on the line 5—5 of FIG. 3.

The sensor 12 is mounted in a mounting base 30 adapted for placement onto the skin of a user. As shown, the mounting base 30 is a generally rectangular pad having an underside surface coated with a suitable pressure sensitive adhesive layer 32, with a peel-off paper strip 34 normally provided to cover and protect the adhesive layer 32, until the sensor set 10 is ready for use. As shown in FIGS. 1 and 2, the mounting base 30 includes upper and lower layers 36 and 38, with the connection portion 24 of the flexible sensor 12 being sandwiched between the layers 36 and 38. The connection portion 24 has a forward section joined to the sensor portion 18 of the sensor 12, which is folded angularly to extend downwardly through a bore 40 formed in the lower base layer 38. In preferred embodiments, the adhesive layer 32 includes an anti-bacterial agent to reduce the chance of infection; however, alternative embodiments may omit the agent. In further alternative embodiments, the mounting base may be other shapes, such as circular, oval, hour-glass, butterfly or the like.

The insertion needle 14 is adapted for slide-fit reception through a needle port 42 formed in the upper base layer 36 and further through the lower bore 40 in the lower base layer 38. As shown, the insertion needle 14 has a sharpened tip 44 and an open slot 46 which extends longitudinally from the tip 44 at the underside of the needle 14 to a position at least within the bore 40 in the lower base layer 36. Above the mounting base 30, the insertion needle 14 may have a full round cross-sectional shape, and may be closed off at a rear end of the needle 14. Further description of the needle 14 and the sensor set 10 are found in U.S. Pat. No. 5,586,553, entitled "TRANSCUTANEOUS SENSOR INSERTION SET" and co-pending U.S. patent application Ser. No. 08/871,831, entitled 'DISPOSABLE SENSOR INSERTION ASSEMBLY," which are herein incorporated by reference.

Figure 6:
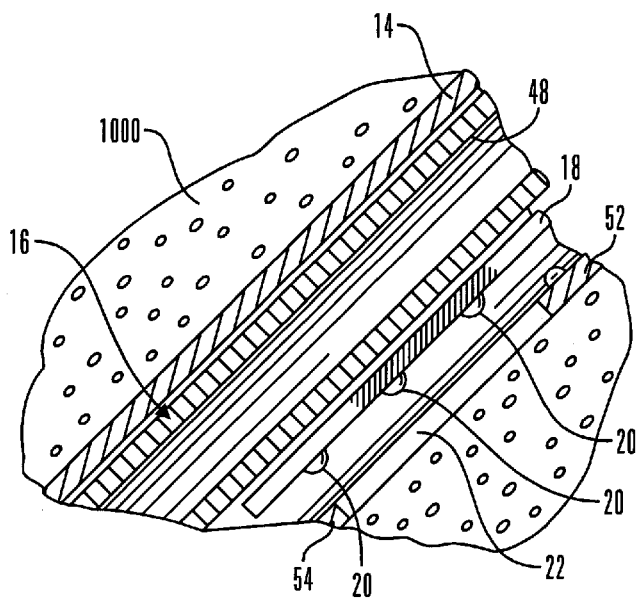
FIG. 6 is an enlarged fragmented sectional view corresponding generally with the encircled region 6 of FIG. 2.
Figure 7:
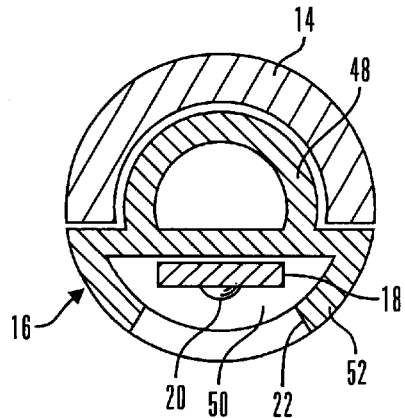
FIG. 7 is an enlarged transverse section taken generally on the line 7—7 of FIG. 2.

The cannula 16 is best illustrated in FIGS. 6 and 7, and includes a first portion 48 having partly-circular cross-section to fit within the insertion needle 14 that extends downwardly from the mounting base 30. In alternative embodiments, the first portion 48 may be formed with a solid core; rather than a hollow core. In preferred embodiments, the cannula 16 is constructed from a suitable medical grade plastic or elastomer, such as polytetrafluoroethylene, silicone, or the like. The cannula 16 also defines an open lumen 50 in a second portion 52 for receiving, protecting and guidably supporting the sensor portion 18 of the sensor 12. The cannula 16 has one end fitted into the bore 40 formed in the lower layer 38 of the mounting base 30, and the cannula 16 is secured to the mounting base 30 by a suitable adhesive, ultrasonic welding, snap fit or other selected attachment method. From the mounting base 30, the cannula 16 extends angularly downwardly with the first portion 48 nested within the insertion needle 14, and terminates slightly before the needle tip 44. At least one window 22 is formed in the lumen 50 near the implanted end 54, in general alignment with the sensor electrodes 20, to permit direct electrode exposure to the user's bodily fluid when the sensor 12 is subcutaneously placed.

In preferred embodiments, shown in FIG. 7, the second portion 52 of the cannula 16 has a partly-circular cross sectional shape which cooperates with the partly-circular shape of the insertion needle 14 to define a substantially full-circle geometry for facilitated insertion through the user's skin. In alternative embodiments, other cross-sections for the needle 14, and first portion 48 and second portion 52 of the cannula 16 may be used, such as rectangular, polygonal, oval or the like. The first portion 48 of the cannula 16 has a generally smaller cross-sectional profile than the second portion 52, for nested sliding reception into the needle 14 to mechanically interlock the needle 14 and cannula 16 to prevent lateral dislocation of the cannula 16 from the insertion needle 14, while permitting longitudinal sliding motion of the needle over the first portion 48 of the cannula 16. The free end of the second portion 52 of the cannula 16 is preferably cut or otherwise set at an oblique angle, as viewed in FIG. 2, to form a continuation of the angle-cut tip 44 of the insertion needle 14.

In use, the sensor set 10 permits quick and easy placement of the sensor portion 18 at a selected site within the body of the user. More specifically, the peel-off strip 34 (see FIG. 1) is removed from the mounting base 30, at which time the mounting base 30 can be pressed onto and seated upon the patient's skin. During this step, the insertion needle 14 pierces the user's skin and carries the protective cannula 16 with the sensor portion 18 to the appropriate placement site. During insertion, the cannula 16 and the needle 14, together, provides a stable support and guide structure to carry the flexible sensor 12 to the desired placement site. When the sensor 12 is placed, with the mounting base 30 seated upon the user's skin, the insertion needle 14 can be slidably withdrawn from the user. During this withdrawal step, the insertion needle 14 slides over the first portion 48 of the protective cannula 16, leaving the sensor portion 18 with electrodes 20 directly exposed to the user's bodily fluids via the window 22. The connection portion 24 is coupled to the monitor 26, so that the sensor 12 can then be used over a prolonged period of time for taking blood chemistry readings, such as blood glucose readings in a diabetic patient. Further description of the needle 14 and the sensor set 10 are found in U.S. Pat. No. 5,586,553, entitled "TRANSCUTANEOUS SENSOR INSERTION SET" and co-pending U.S. patent application Ser. No. 08/871,831, entitled 'DISPOSABLE SENSOR INSERTION ASSEMBLY," which are herein incorporated by reference.

In use, sensor sets are generally inserted and used for a period of days or more. Over time it has been found that the performance of the sensor sets degrades in some cases, and that the amount of time that a sensor set can be used varies from individual user to individual user. In sensor sets 10 that include a sensor 12, bodily fluids may begin to form a pool 1000 around the exposed sensor 12 and cannula 16 after insertion and implantation (see FIGS. 2 and 7). This pool 1000 may continue to expand and accumulate over time. Eventually, the presence of the pool 1000 degrades and affects the performance and accuracy of the sensor 12. It is believed that the pool 1000 dilutes the concentrations of various compositions, such as glucose or the like, and may create a "lag" response in the user's other bodily fluids as they enter and mingle with the pool 1000. Thus, the sensor 12 becomes less accurate for detecting small changes in the concentration levels, and tends to report more of a steady state value. In addition, the pool 1000 is relatively stagnant and this increases the possibility of an infection developing. As discussed above, it has been observed that the rate of performance degradation varies from individual to individual, and that when a sensor 12 is removed from the body of an individual user, and tested, the sensor 12 is capable of providing the required accuracy of determining the level of characteristics in a calibration and/or test solution of a known level. Thus, the variation in the amount of time a sensor set 10 can remain in a user's body is dependent on the user and not the sensor 12; and, once fluid is removed from the pool 1000, nominal sensor 12 accuracy is restored and the stagnant fluid is no longer present to provide an opportunity for an infection to develop. Therefore, there is a need to remove the bodily fluid forming the pool 1000 to extend the useful life of a sensor set 10 and to reduce the possibility of developing an infection.

Figure 8:
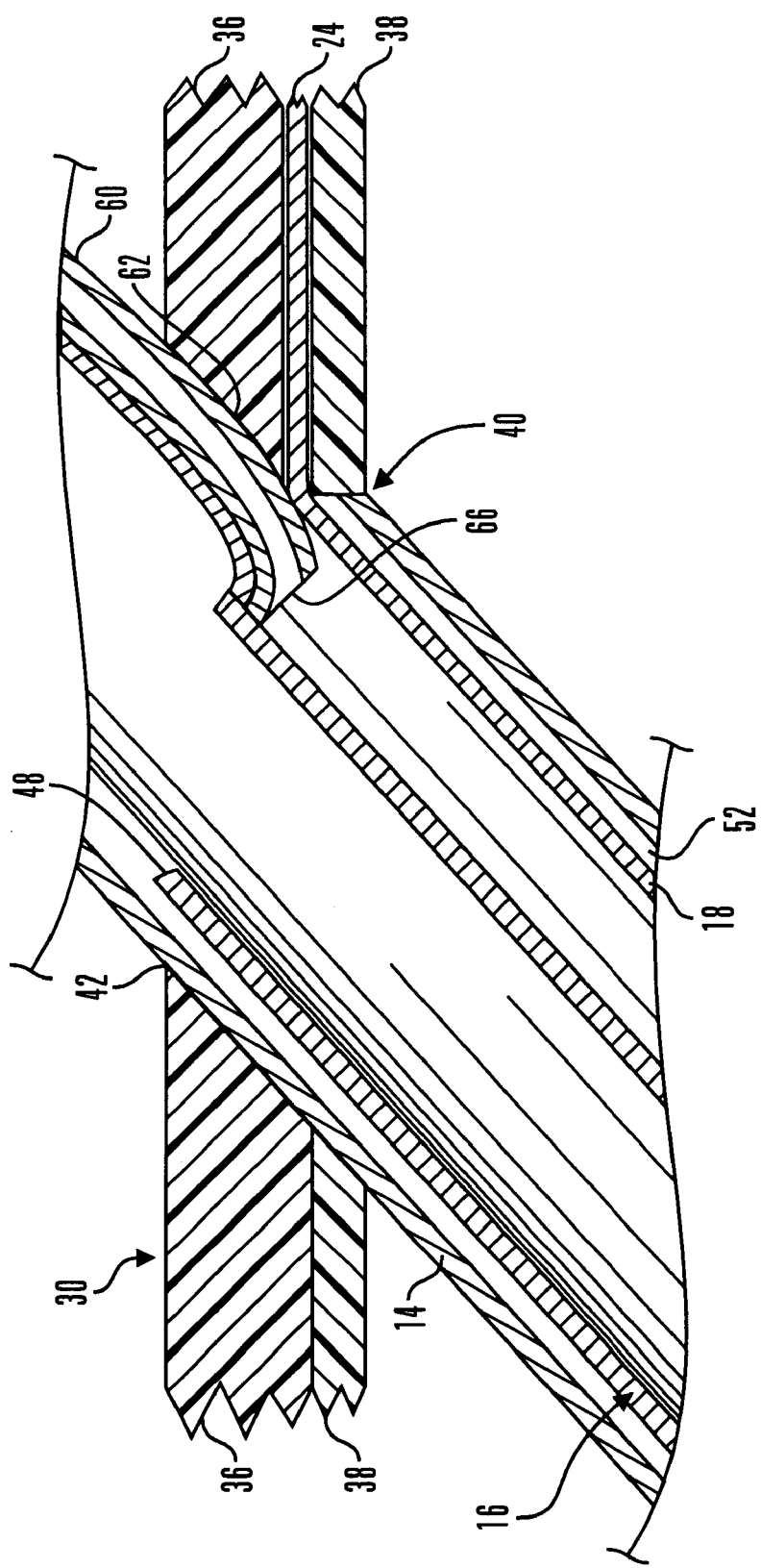
FIG. 8 is an enlarged transverse section taken generally on the line 8—8 of FIG. 2.

As shown in FIGS. 1, 2 and 8, the sensor set 10 includes an additional externally extending lumen 60 in fluid communication with the second portion 52 of the cannula 16. The additional lumen 60 is coupled to the mounting base 30 and communicates with the cannula 16 through a fluid conduit 62 formed in the mounting base 30. In alternative embodiments, the fluid conduit 62 may be formed as an extension of the lumen 60 that is inserted through a bore formed in the mounting base 30 or the like. One end of the lumen 60 is coupled and secured to the mounting base 30 by adhesives, ultrasonic welding, snap fit or other suitable methods. The other end of the lumen 60 includes a syringe port and guide 64 that is used to guide a syringe (not shown) or the like to the lumen 60 to provide fluid communication with the cannula 16. In preferred embodiments, the lumen 60, conduit 62 and the syringe port 64 are formed from a suitable medical-grade plastic material that is biocompatible. However, in alternative embodiments, the lumen 60, conduit 62 and the syringe port 64 are formed out of other suitable materials, such as metal, glass, composites or the like. In further embodiments, the lumen 60 may be removable from the mounting base 30 when not in use and/or adapted for easy attachment to the mounting base 30 when needed for withdrawing fluids from the body of the user. The lumen 60 may also include an end (not shown) configured to have a snap or friction fit and sufficient structural strength to facilitate attachment to the conduit 62 and the mounting base 30.

In preferred embodiments, the end of the second portion 52 of the cannula 16 includes a septum 66 that provides a seal to substantially inhibit the incursion of external contaminants, such as bacteria, debris, or the like, from entering the cannula 16 and contaminating the placement site. This reduces the likelihood of developing an infection through contact with the external environment. In further embodiments, the lumen 60 and conduit 62 may include an anti-bacterial agent on the interior surface of the lumen 60 or actually formed as an integral part of the lumen 60 and conduit 62 material to further minimize the chance of an infection.

To remove fluid in the pool 1000 from the area surrounding the cannula 16 and the sensor portion 18 of the sensor 12, the user attaches the lumen 60 and syringe port 64 to the end of the conduit 62 on the mounting base 30 (although in alternative embodiments, the lumen 60 and syringe port 64 may be already in place or formed as part of the set 10). Next, the user introduces a needle of a syringe (not shown), or the like, into the syringe port and guide 64 and pierces the septum 66. The user then generates a vacuum pressure in the syringe, or the like, and this draws out the bodily fluid forming the pool 1000 surrounding the cannula 16 and sensor 12. When sufficient fluid is extracted, the syringe is withdrawn from the syringe port and guide 64. Finally, the lumen 60 and syringe port and guide 64 can be removed. In alternative embodiments, the withdrawn fluid may be used to calibrate and/or control check the sensor 12.

In particular embodiments, to verify that sufficient fluid has been removed, another syringe or medication delivery device may be connected to the lumen 60 and syringe port and guide 64, and a small amount of calibrating fluid is introduced. The sensor 12 output is then analyzed to determine if sufficient fluid was withdrawn and the sensor 12 is still operating within nominal parameters. After the test, the small amount of fluid can be withdrawn, or left at the subcutaneous placement site, if small enough not to effect future readings. The syringe or medication delivery device is then removed, and the user continues to use the sensor set for the full period of extended implantation. After removal of the test solution syringe, the lumen 60 and syringe port and guide 64 can be removed.

In other embodiments, the lumen 60 and conduit 62 may be used to introduce fluids that are capable of cleaning or recharging the sensor 12 for longer period of use. The user would introduce a non-toxic cleaning agent or recharging fluid, and then withdraw the introduced fluid after a specified period of time.

In alternative embodiments, the lumen 60, the syringe port and guide 64, and septum 66 may be omitted. The conduit 62 is filled with a wicking material (not shown) and the opening of the conduit 62 at the surface of the mounting base 30 is closed off with a filter (not shown) that prevents external contaminants from entering the wicking material and the cannula 16. In preferred embodiments, the filter is porous enough to allow the excess fluid removed by the wicking process to evaporate out of the conduit 62. However, in alternative embodiments, the filter acts as a septum, and a syringe or the like is periodically introduced into the conduit 62 to remove the accumulated fluid. In further alternative embodiments, the wicked away fluid may be used to calibrate and/or control check the sensor 12.

In further embodiments, prior to removal of the sensor set 10, the user may attach a syringe or the like to the lumen 60 or the conduit 62, and introduce an anti-bacterial solution, anti-biotic and/or healing promoting agent to the placement site to facilitate healing and to reduce the risk of infection after removal of the sensor set. Additional fluids that can be introduced in still other embodiments include anti-inflammatory agents, cleaning agents and sensor recharging agents.

In still further embodiments, the excess fluid may be removed from the pool 1000 prior to removal of the sensor set and/or prior to introduction of the anti-bacterial fluid.

In yet another embodiments, a pre-evacuated vacuum tube, or the like, may be used instead of a syringe. In addition, a step motor type pump, continuous pump, automated pump or the like, may be used in place of the syringe for regular withdrawal of the fluid in the pool 1000. In still another embodiment, the fluid is regularly withdrawn using a fluid path that causes the withdrawn fluid to flow over the sensor 12 to assure a regular change of fluid coming in contact with the sensor 12.

In further embodiments of the present invention, the lumen 60 and conduit 62 may be added to an infusion set (not shown) to facilitate removal of fluid that may build up around the outlet of the infusion cannula (not shown) that could impede the infusion or distribution of a medication at a subcutaneous placement site. In addition, the first portion 48 of the cannula 16 can be hollow, as shown in the FIGS., to form a second lumen available to deliver medication and/or sensor calibration fluid to the vicinity of the electrodes 20, or alternately to withdraw user bodily fluids. It may also be used in conjunction with the other lumen 52 in the cannula to facilitate multiple flow paths or cooperative flow, such as the introduction and extraction of fluids at the same time.

Particular embodiments of the present invention facilitate introduction of a fluid to a placement site as well as extraction of a fluid from the site. Examples of fluids that are beneficially introduced to a placement site in accordance with the inventive method include, without limitation, anti-biotic and anti-inflammatory solutions, solutions including healing agents, cleaning agents and sensor recharging agents, as well as solutions containing insulin and/or insulin analogs, saline solutions. Additional solutions that are beneficially supplied to a placement site according to the inventive method include sensor calibration solutions, i.e., solutions that have known levels of the bodily characteristic that is determined by the sensor at the placement site. For example, a calibration solutions for use with a glucose sensor contains a predetermined concentration of glucose.

According to embodiments of the present invention, a sensor set as described above is mounted onto the user's skin above the desired placement site, and the placement site is contacted with the sensor set. Once contact with the placement site has been established, the fluid is supplied to the placement site via the sensor set.

In particular embodiments of the inventive method, the sensor set employed includes an externally extending conduit that is in fluid communication with the port defined in the cannula. In these embodiments, the fluid is introduced through the externally extending conduit 62 into the lumen 60 of the sensor set and thence to the placement site. More specific embodiments employ sensor sets that also include an insertion device that facilitates insertion of the cannula to contact the placement site.

In other particular embodiments of the inventive method, the fluid is introduced directly through the port of the lumen 60 of the sensor set. In such embodiments, inclusion of an externally extending conduit in the sensor set is optional.

Fluids are supplied to the placement site according to specific embodiments of the inventive method periodically in predetermined amounts. A preferred source of the fluid to be supplied, in such embodiments, is an external infusion pump device. Such an infusion pump can be provided as a separate device, or can be provided in combination with one or more other elements, for example in combination with an electronic transmitter module that is connected to the sensor.

Useful infusion pumps include, for example, propellant-driven pumps. Particular propellant-driven pumps are those that include a supply of a propellant gas, such as a freon, air, nitrogen or $CO_2$, as well as those that generate a propellant gas, for example by electrolysis of water or another liquid. The source of the propellant (i.e., the propellant gas or the liquid from which the propellant gas is generated) can be a separate receptacle, or a sub-receptacle which in turn is located within the source of the fluid to be supplied to the placement site. A source of the propellant can also be located in or affixed to the sensor set itself; however, the resulting increase in the volume of the sensor set may be less desirable. The fluid can also be provided from receptacles that employ springs, elastomeric materials or the like that exert a force to expel and supply the fluid.

Other preferred sources of the fluid to be supplied to the placement site include finger-activated pumps, as well as blisters which, in more specific embodiments, are formed as part of the sensor set. According to embodiments of the inventive method that employ such sources, a user activates the pump or presses the blister, thus urging the fluid through the sensor set to the placement site. Additional devices that can be used according to such embodiments of the inventive method include bolus pen delivery units.

According to further preferred embodiments of the inventive method, the selected fluid is supplied to the placement site from a disposable source. Such disposable sources include, for example, syringes, as well as small blisters containing the selected fluid that are connectable to the sensor set and that the user ruptures by squeezing.

Introduction of a fluid to a placement site according to embodiments of the inventive methods is particularly beneficial when the sensor at the placement site requires calibration upon insertion and/or at subsequent periods after insertion. Glucose sensors are exemplary of sensors typically requiring such calibration; sensor error must be reduced to minimize the risk of inaccurate insulin dosage when the sensor output is used to determine the amount of insulin to be delivered, especially if such delivery is automatic. Introduction of a calibration solution to the placement site by embodiments of the present invention resolves these concerns. In addition, introduction of a fluid in accordance with embodiments of the present invention can provide a further advantage of creating a fluid cushion to minimize motion artifacts of the sensor.

According to one particular embodiment using a calibration solution, the solution is simply supplied via lumen 60 to pass over the sensor electrodes 20 and exits out of the end of the cannula of the sensor set. In this embodiment, if desired, window 22 can be omitted in order to ensure that the substantially all of the fluid passes over the sensor electrodes and exits out of the end of the cannula.

Figure 12:
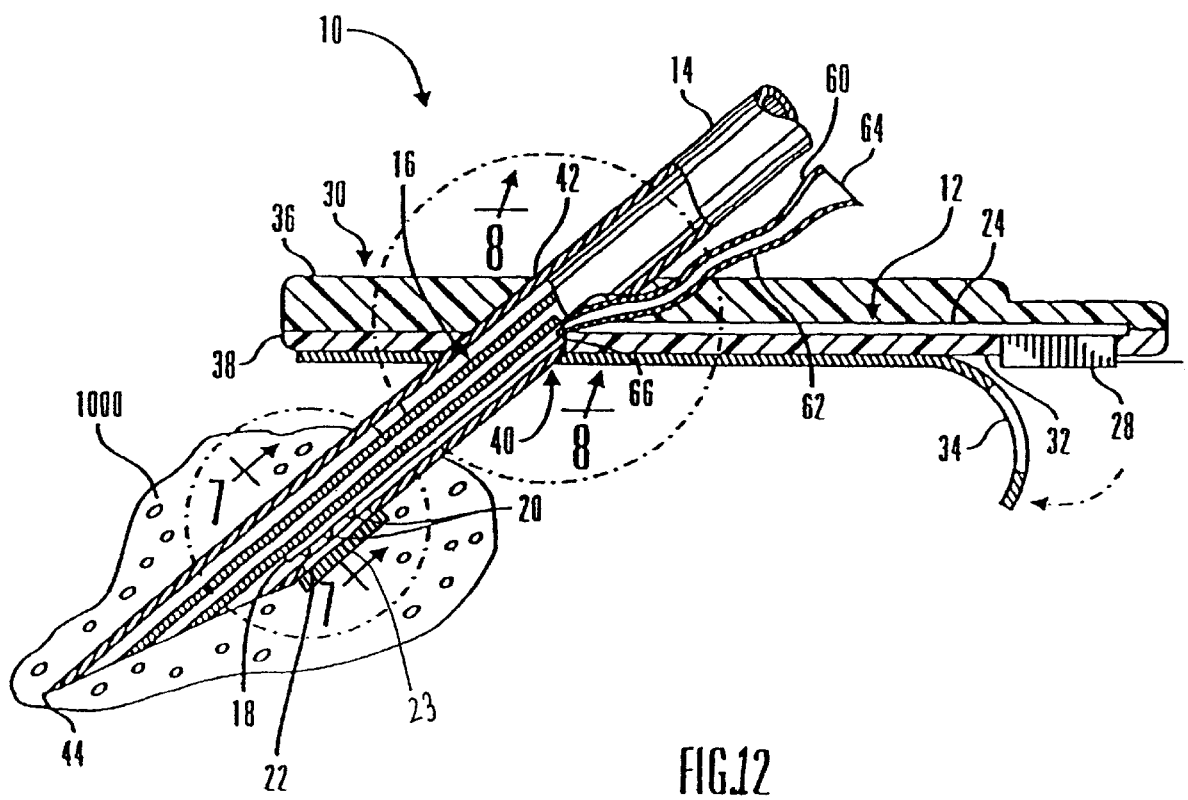
FIG. 12 is an alternative embodiment of the sensor set of FIG. 2 including a membrane covering the window in the cannula, the membrane being permeable to the agent, such as glucose, which is to be detected by the sensor electrodes.

In an alternative more specific embodiment, illustrated in FIG. 12, the selected fluid is provided to the placement site via a modification of the device of FIG. 2 in which a membrane 23 covers window 22 over sensors electrodes 20. In this embodiment, the membrane 23 permits the passage of the agent, such as glucose, which is to be detected by the sensor electrodes.

Figure 9:
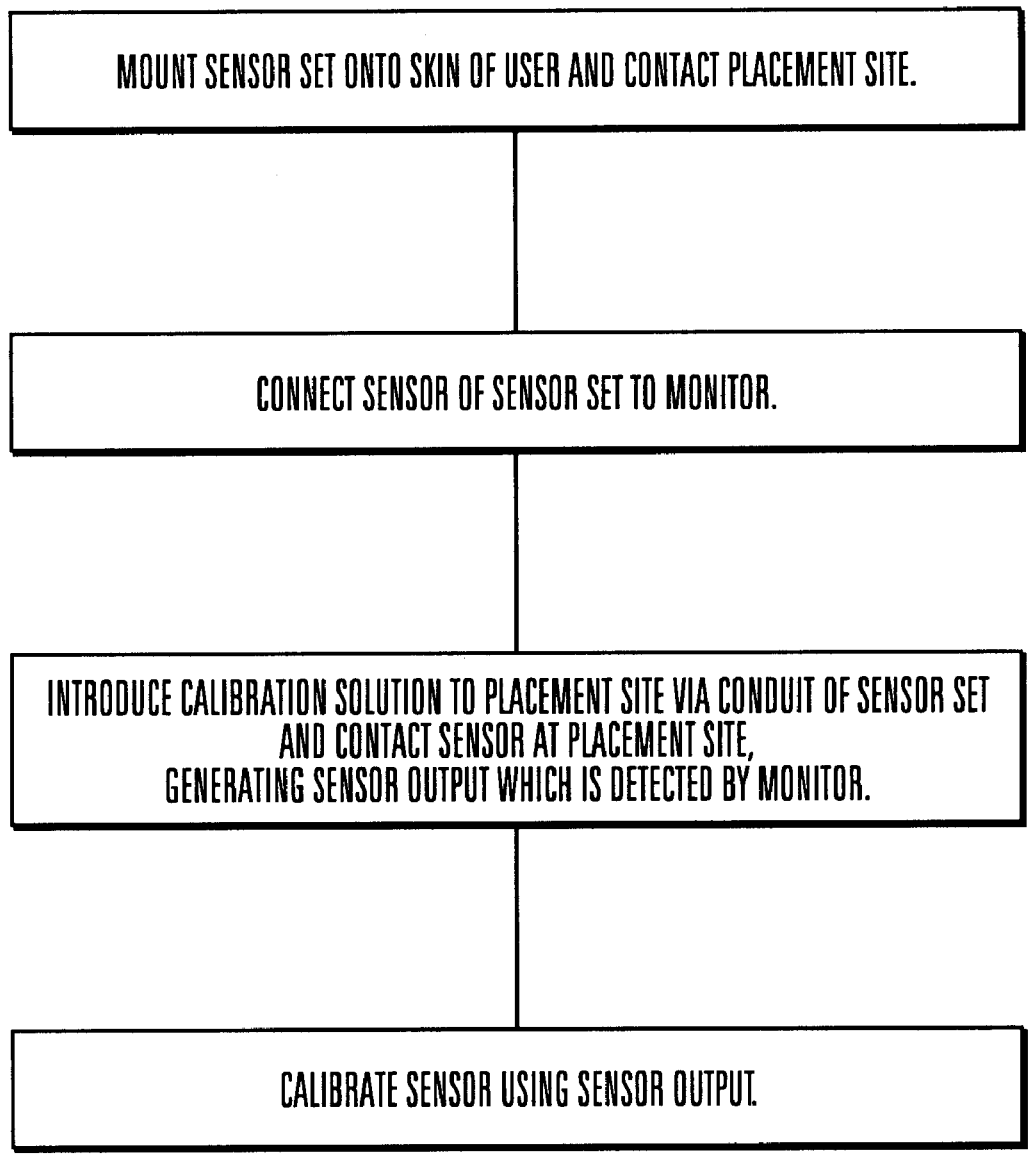
FIG. 9 is a flowchart illustrating an embodiment of a fluid supply method in accordance with an embodiment of the present invention including a calibration step.

In carrying out embodiments of the foregoing calibration method according to embodiments of the present invention (see FIG. 9), the selected fluid is supplied to the site either periodically or a single time after attachment of the sensor set on the user's skin and establishment of contact between the sensor and the placement site. For periodic supply using an external infusion pump, the infusion pump is activated (e.g. by electrical means) for a fixed time to cause a small but fixed amount of the fluid to pass through the lumen 60 and over the sensors 20, forcing any indwelling bodily fluid out of the sensor set and away from contact with the sensor electrodes. The sensor output is then used to calibrate the sensor. In embodiments in which a membrane is disposed over the window 22, within several minutes, the body characteristic, such as glucose level, in the fluid in contact with the sensors 20 and in the bodily fluid external to the implanted sensor will equilibrate, so that measurements made thereafter will reflect the body characteristic of the bodily fluid, with only a short time differential.

In another alternative embodiment, a valve, such as a flapper valve, is provided at or near the distal end of cannula 16. The valve permits the fluid to be pumped or flowed across the sensor. A flapper valve proximal to the sensor area and opening inward closes when the fluid is released, but opens and provides a second port on the proximal side relative to the sensors 20, facilitating circulation of bodily fluid (e.g., interstitial fluid) from the placement site across the sensors.

Calibration preferably is carried out according to the inventive method at the time of sensor insertion, and periodically throughout the stabilization period, and can be terminated, for example, when two or more sequential calibrations are within a predetermined tolerance band. Thereafter calibration can be carried out as often as may be appropriate (e.g. daily or more often if needed) and at any preset alarm level.

Exemplary embodiments of the inventive calibration method are beneficially combined with the administration of insulin to patients in need of such treatment. In the combined treatment, insulin is supplied to the patient as needed, for example periodically or continuously. The patient's glucose level is monitored using a sensor set as described herein in contact with a placement site. At regular intervals, the insulin supply is suspended, and a calibration solution is supplied to the placement site to calibrate the sensor in contact with the site. The insulin and the calibration solution can be provided via the same device (i.e., via a common sensor set), or the insulin can be supplied using a separate device.

To accomplish the various fluid supply methods according to embodiments of the present invention, kits are provided that include a sensor set as described herein together with a source of the fluid to be supplied. Further embodiments may also include a delivery device for the fluid. Preferred fluid sources, as mentioned above, include external infusion pumps and disposable blisters, as well as containers of the fluid to be supplied together with a syringe. Delivery devices include, without limitations, conduits, needles of syringes, and the like.

Figure 10:
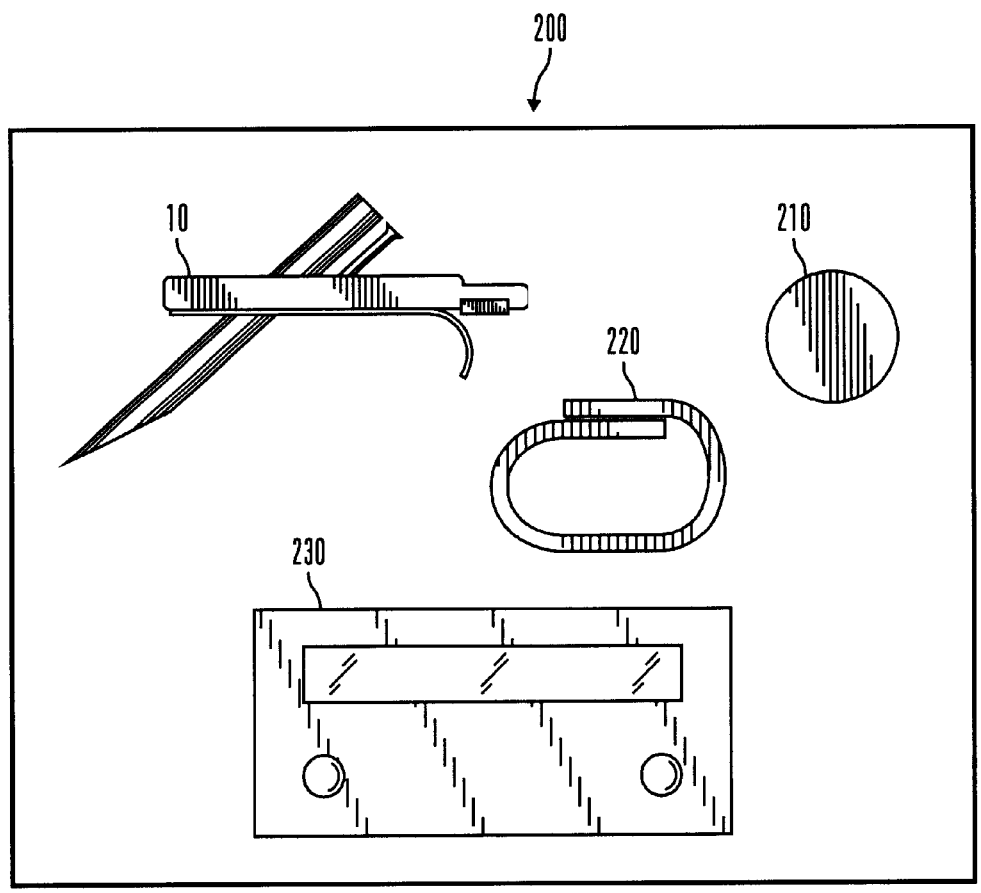
FIG. 10 is a schematic diagram of an embodiment of a kit according to an embodiment of the present invention including a monitor.
Figure 11:
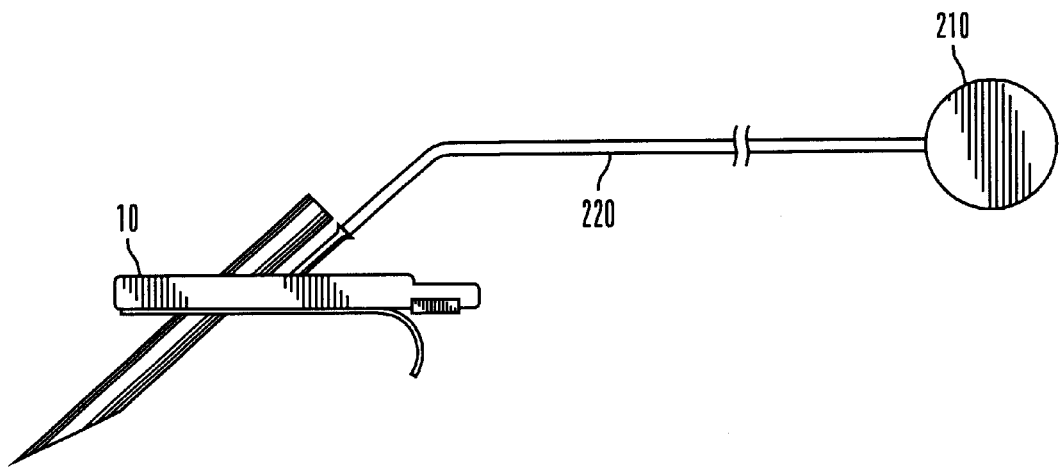
FIG. 11 is a schematic diagram illustrating the connection of an external fluid source and an embodiment of a sensor set useful according to embodiments of the present invention.

According to a more specific embodiment, the inventive kits also include a monitor that is electrically connectable to the sensor (via an appropriate connection portion) for use in monitoring the desired body characteristic, such as glucose level, of the user. As shown in FIG. 10, kit 200 includes a sensor set 10, a fluid source 210 (as illustrated, an external infusion pump), a delivery device 220 connecting the pump and the sensor set, and a monitor 230 which is electrically connectable to the sensor of sensor set 10. In FIG. 11, the connection of sensor set 10 and pump 210 via delivery device 220 is illustrated.

According to additional preferred embodiments of kits useful for sensor calibration, the kits further include a signaling device that informs a user when the calibration solution has been supplied to the placement site. Examples of such devices include, without limitation, visual displays such as LEDs or LCDs, audio signals such as pulse tones, and the like. The signaling device can be incorporated into the sensor set, combined with the source of the fluid, or provided as a separate device.

In addition to the sensor sets described above, other sensor sets can readily be adapted to facilitate supply of a fluid to a placement site in accordance with the principles set forth herein. In particular, the sensor sets disclosed and described in U.S. Provisional Patent Application Ser. No. 60/103,812, filed Oct. 8, 1998, to Purvis, entitled "Telemetered Characteristic Monitor System and Method of Using the Same," (attorney docket no. PD-0291PRO) and in U.S. patent application Ser. No. 09/377,472, filed Aug. 19, 1999, to Mann et al., entitled "Telemetered Characteristic Monitor System and Method of Using the Same," (attorney docket no. PD-0291), the entire disclosures of each of which are incorporated herein by reference, can be adapted in accordance with the present invention, for example by provision of lumen 60 and conduit 62 as taught herein. Methods using such sensor sets, and kits including such sensor sets as well as associated elements such as telemetered characteristic monitor transmitter devices, are intended to be encompassed within the scope of the present invention. Thus, in further alternative embodiments of the present invention, the sensors can be of a type that is used on the external surface of the skin or placed below the skin layer of the user. Preferred embodiments of such surface mounted sensors will utilize interstitial fluid harvested from underneath the skin.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method of supplying a fluid to a placement site, the method comprising the steps of:
   a) mounting a sensor set onto a skin of a user and contacting a placement site with the sensor set, the sensor set including:
      i) a base to secure the sensor set to the skin of the user;
      ii) a cannula coupled to and extending from the base, wherein the cannula has at least one lumen with an end for fluid communication with the placement site, wherein the cannula also has at least one port formed near another end of the lumen opposite the end for fluid communication;
      iii) an insertion device operatively coupled to the sensor set and the cannula to facilitate insertion of the cannula to contact the placement site;
      iv) an externally extending conduit in fluid communication with the at least one port of the cannula; and
      v) a sensor having a sensor portion exposed by the at least one port in the at least one lumen of the cannula to determine a body characteristic of the user at the placement site; and
   b) introducing a fluid through the externally extending conduit and the lumen to the placement site.

2. The method of claim 1, wherein the fluid is supplied periodically in a predetermined amount.

3. The method of claim 2, wherein the fluid is supplied from an external infusion pump device.

4. The method of claim 1, wherein the fluid is supplied from a disposable source.

5. The method of claim 1, wherein the fluid includes an ingredient selected from the group consisting of a healing agent, an antibiotic, an anti-inflammatory agent, a cleaning agent, a sensor recharging agent, an insulin, an insulin analog, saline and glucose.

6. The method of claim 1, wherein the fluid is a calibration solution having a known level of the body characteristic of the user.

7. The method of claim 6, wherein the body characteristic is the glucose level in a bodily fluid of the user, and wherein the calibration solution comprises a predetermined concentration of glucose.

8. The method of claim 7, wherein the bodily fluid is blood or interstitial fluid.

9. The method of claim 1, wherein the placement site is a subcutaneous, dermal, intraperitoneal or peritoneal site.

10. The method of claim 9, wherein the placement site is a subcutaneous site.

11. A method of supplying a fluid to a placement site, the method comprising the steps of:
   a) mounting a sensor set onto a skin of a user and contacting therewith a placement site, the sensor set including:
      i) a base to secure the sensor set to the skin of the user;
      ii) a cannula coupled to and extending from the base, wherein the cannula has at least one lumen with an end for fluid communication with the placement site, wherein the cannula also has at least one port formed near another end of the lumen opposite the end for fluid communication; and
      iii) a sensor having a sensor portion exposed by the at least one port in the at least one lumen of the cannula to determine a body characteristic of the user at the placement site; and
   b) introducing a fluid through the port of the lumen to the placement site,
   wherein the sensor set further comprises an insertion device operatively coupled to the set and the cannula to facilitate insertion of the cannula to contact the placement site.

12. A method of supplying a fluid to a placement site, the method comprising the steps of:
   a) mounting a sensor set onto a skin of a user and contacting therewith a placement site, the sensor set including:
      i) a base to secure the sensor set to the skin of the user;
      ii) a cannula coupled to and extending from the base, wherein the cannula has at least one lumen with an end for fluid communication with the placement site, wherein the cannula also has at least one port formed near another end of the lumen opposite the end for fluid communication; and
      iii) a sensor having a sensor portion exposed by the at least one port in the at least one lumen of the cannula to determine a body characteristic of the user at the placement site; and
   b) introducing a fluid through the port of the lumen to the placement site,
   wherein the sensor set further comprises a septum disposed adjacent the at least one port of the cannula, and wherein the fluid is introduced through the septum and the lumen to the placement site.

13. A method of supplying a fluid to a placement site, the method comprising the steps of:
   a) mounting a sensor set onto a skin of a user and contacting therewith a placement site, the sensor set including:
      i) a base to secure the sensor set to the skin of the user;
      ii) a cannula coupled to and extending from the base, wherein the cannula has at least one lumen with an end for fluid communication with the placement site, wherein the cannula also has at least one port formed near another end of the lumen opposite the end for fluid communication; and
      iii) a sensor having a sensor portion exposed by the at least one port in the at least one lumen of the cannula to determine a body characteristic of the user at the placement site; and
   b) introducing a fluid through the port of the lumen to the placement site,
   wherein the sensor set further comprises an externally extending conduit in fluid communication with the at least one port of the cannula, and wherein the fluid is introduced through the externally extending conduit and the lumen to the placement site.

14. A method of supplying a fluid to a placement site, the method comprising the steps of:
   a) mounting a sensor set onto a skin of a user and contacting therewith a placement site, the sensor set including:
      i) a base to secure the sensor set to the skin of the user;
      ii) a cannula coupled to and extending from the base, wherein the cannula has at least one lumen with an end for fluid communication with the placement site, wherein the cannula also has at least one port formed near another end of the lumen opposite the end for fluid communication;
      iii) an externally extending conduit in fluid communication with the at least one port of the cannula; and
      iv) a sensor having a sensor portion exposed by the at least one port in the at least one lumen of the cannula to determine a body characteristic of the user at the placement site; and
   b) introducing a fluid through the externally extending conduit and the lumen to the placement site.

15. A method of calibrating a sensor which is placed at a placement site and which is adapted to determine a body characteristic of a user, the method comprising the steps of:

a) mounting a sensor set onto a skin of a user and contacting therewith a placement site, the sensor set including:
   i) a base to secure the sensor set to the skin of the user;
   ii) a cannula coupled to and extending from the base, wherein the cannula has at least one lumen with an end for fluid communication with the placement site, wherein the cannula also has at least one port formed near another end of the lumen opposite the end for fluid communication;
   iii) an insertion device operatively coupled to the sensor set and the cannula to facilitate insertion of the cannula to contact the placement site;
   iv) an externally extending conduit in fluid communication with the at least one port of the cannula; and
   v) a sensor having a connection portion coupled to the sensor set, and a sensor portion exposed by the at least one port in the at least one lumen of the cannula to determine the characteristic of the user at the placement site;
b) electrically connecting the connection portion of the sensor to a monitor for monitoring the characteristic of the user;
c) introducing a predetermined quantity of a calibration solution having a known level of the characteristic of the user through the externally extending conduit to the sensor portion of the sensor, whereby a sensor output is generated and detected by the monitor; and
d) calibrating the sensor using the sensor output.

16. The method of claim 15, wherein the body characteristic is the glucose level in a bodily fluid of the user, and wherein the calibration solution comprises a predetermined concentration of glucose.

17. The method of claim 16, wherein the bodily fluid is blood or interstitial fluid.

18. The method of claim 15, wherein the placement site is a subcutaneous, dermal, intraperitoneal or peritoneal site.

19. The method of claim 18, wherein the placement site is a subcutaneous site.

20. A kit for supplying fluid to a placement site, the kit, in appropriate packaging, comprising:
a) a sensor set comprising:
   i) a base to secure the sensor set to the skin of the user;
   ii) a cannula coupled to and extending from the base, wherein the cannula has at least one lumen with an end for fluid communication with the placement site, wherein the cannula also has at least one port formed near another end of the lumen opposite the end for fluid communication;
   iii) an insertion device operatively coupled to the sensor set and the cannula to facilitate insertion of the cannula to contact the placement site;
   iv) an externally extending conduit in fluid communication with the at least one port of the cannula; and
   v) a sensor having a sensor portion exposed by the at least one port in the at least one lumen of the cannula to determine a body characteristic of the user at the placement site;
b) a source of fluid to be supplied to the placement site; and
c) a delivery device by which the fluid is introduced into the externally extending conduit and thence to the placement site.

21. The kit of claim 20, wherein the source of fluid is an external infusion pump.

22. The kit of claim 20, wherein the source of fluid is a disposable bubble.

23. The kit of claim 20, wherein the source of fluid is a container of fluid and wherein the delivery device is a syringe.

24. The kit of claim 20, wherein the sensor has a connection portion coupled to the sensor set, and wherein the kit further comprises a monitor that is electrically connectable to the connection portion of the sensor.

25. A kit for supplying a fluid to a placement site, the kit, in appropriate packaging, comprising:
a) a sensor set comprising:
   i) a base to secure the sensor set to the skin of a user;
   ii) a cannula coupled to and extending from the base, wherein the cannula has at least one lumen with an end for fluid communication with the placement site, wherein the cannula also has at least one port formed near another end of the lumen opposite the end for fluid communication;
   iii) an externally extending conduit in fluid communication with the at least one port of the cannula; and
   iv) a sensor having a sensor portion exposed by the at least one port in the at least one lumen of the cannula to determine a body characteristic of the user at the placement site;
b) a source of fluid to be supplied to the placement site; and
c) a delivery device by which the fluid is introduced into the externally extending conduit and thence to the placement site.

26. A kit for calibrating a sensor which is placed at a placement site and which is adapted to determine a body characteristic of a user, the kit, in appropriate packaging, comprising:
a) a sensor set comprising:
   i) a base to secure the sensor set to the skin of the user;
   ii) a cannula coupled to and extending from the base, wherein the cannula has at least one lumen with an end for fluid communication with the placement site, wherein the cannula also has at least one port formed near another end of the lumen opposite the end for fluid communication;
   iii) an insertion device operatively coupled to the sensor set and the cannula to facilitate insertion of the cannula to contact the placement site;
   iv) an externally extending conduit in fluid communication with the at least one port of the cannula; and
   v) a sensor having a connection portion coupled to the sensor set, and a sensor portion exposed by the at least one port in the at least one lumen of the cannula to determine the characteristic of the user at the placement site;
b) a source of a predetermined quantity of a calibration solution having a known level of the characteristic of the user; and
c) a delivery device by which the predetermined quantity of the calibration solution is introduced into the externally extending conduit and thence to the sensor at the placement site.

27. The kit of claim 26, wherein the body characteristic of the user is the glucose level in a bodily fluid of the user, and wherein the calibration solution comprises a predetermined concentration of glucose.

28. The kit of claim 26, wherein the source of the calibration solution is an external infusion pump.

29. The kit of claim 26, wherein the source of the calibration solution is a disposable bubble.

30. The kit of claim 26, wherein the source of the calibration solution is a container of fluid and wherein the delivery device is a syringe.

31. The kit of claim 26, wherein the sensor has a connection portion coupled to the sensor set, and wherein the kit further comprises a monitor that is electrically connectable to the connection portion of the sensor.

32. A system for supplying fluid to a placement site, the system comprising:
   a) a sensor set comprising:
      i) a base to secure the sensor set to the skin of the user;
      ii) a cannula coupled to and extending from the base, wherein the cannula has at least one lumen with an end for fluid communication with the placement site, wherein the cannula also has at least one port formed near another end of the lumen opposite the end for fluid communication;
      iii) an insertion device operatively coupled to the sensor set and the cannula to facilitate insertion of the cannula to contact the placement site; and
      iv) a sensor having a sensor portion exposed by the at least one port in the at least one lumen of the cannula to determine a body characteristic of the user at the placement site;
   b) a source of fluid to be supplied to the placement site; and
   c) a delivery device by which the fluid is introduced into the cannula and thence to the placement site.

33. The system of claim 32, wherein the source of fluid is an external infusion pump.

34. The system of claim 32, wherein the source of fluid is a disposable bubble.

35. The system of claim 32, wherein the source of fluid is a container of fluid and wherein the delivery device is a syringe.

36. The system of claim 32, wherein the sensor has a connection portion coupled to the sensor set, and wherein the system further comprises a monitor that is electrically connectable to the connection portion of the sensor.

37. A system for calibrating a sensor which is placed at a placement site and which is adapted to determine a body characteristic of a user, the system comprising:
   a) a sensor set comprising:
      i) a base to secure the sensor set to the skin of the user;
      ii) a cannula coupled to and extending from the base, wherein the cannula has at least one lumen with an end for fluid communication with the placement site, wherein the cannula also has at least one port formed near another end of the lumen opposite the end for fluid communication;
      iii) an insertion device operatively coupled to the sensor set and the cannula to facilitate insertion of the cannula to contact the placement site; and
      iv) a sensor having a connection portion coupled to the sensor set, and a sensor portion exposed by the at least one port in the at least one lumen of the cannula to determine the characteristic of the user at the placement site;
   b) a source of a predetermined quantity of a calibration solution having a known level of the characteristic of the user; and
   c) a delivery device by which the predetermined quantity of the calibration solution is introduced into the cannula and thence to the sensor at the placement site.

38. The system of claim 37 wherein the body characteristic of the user is the glucose level in a bodily fluid of the user, and wherein the calibration solution comprises a predetermined concentration of glucose.

39. The system of claim 37, wherein the source of the calibration solution is an external infusion pump.

40. The system of claim 37, wherein the source of the calibration solution is a disposable bubble.

41. The system of claim 37, wherein the source of the calibration solution is a container of fluid and wherein the delivery device is a syringe.

42. The system of claim 37, wherein the sensor has a connection portion coupled to the sensor set, and wherein the system further comprises a monitor that is electrically connectable to the connection portion of the sensor.

43. A system for supplying fluid to a placement site, the system comprising:
   a) a sensor set comprising:
      b) a base to secure the sensor set to the skin of the user;
      ii) a cannula coupled to and extending from the base, wherein the cannula has at least one lumen with an end for fluid communication with the placement site, wherein the cannula also has at least one port formed near another end of the lumen opposite the end for fluid communication;
      iii) an insertion device operatively coupled to the sensor set and the cannula to facilitate insertion of the cannula to contact the placement site;
      iv) an externally extending conduit in fluid communication with the at least one port of the cannula;
      v) a sensor having a sensor portion exposed by the at least one port in the at least one lumen of the cannula to determine a body characteristic of the user at the placement site; and
      vi) a membrane disposed over the at least one port in the at least one lumen of the cannula, the membrane permitting passage of at least one agent to be detected by the sensor;
   b) a source of fluid to be supplied to the placement site; and
   c) a delivery device by which the fluid is introduced into the externally extending conduit and thence to the placement site.

44. The system of claim 43 wherein the membrane permits the passage of glucose.

45. A method of supplying fluid to a placement site, the method comprising the steps of
   a) mounting a sensor set onto a skin of a user and contacting a placement site with the sensor set, the sensor set including:
      i) a base to secure the sensor set to the skin of the user;
      ii) a cannula coupled to and extending from the base, wherein the cannula has at least one lumen with an end for fluid communication with the placement site, wherein the cannula also has at least one port formed near another end of the lumen opposite the end for fluid communication;
      iii) an insertion device operatively coupled to the sensor set and the cannula to facilitate insertion of the cannula to contact the placement site;
      iv) an externally extending conduit in fluid communication with the at least one port of the cannula;
      v) a sensor having a sensor portion exposed by the at least one port in the at least one lumen of the cannula to determine a body characteristic of the user at the placement site; and
      vi) a membrane disposed over the at least one port in the at least one lumen of the cannula, the membrane permitting passage of at least one agent to be detected by the sensor; and
   b) introducing a fluid through the externally extending conduit and the lumen to the placement site.

* * * * *